United States Patent
Aubrun-Sonneville et al.

(10) Patent No.: US 7,879,345 B2
(45) Date of Patent: *Feb. 1, 2011

(54) COMPOSITION CONTAINING AN AMPHIPHILIC POLYMER, USES THEREOF

(75) Inventors: Odile Aubrun-Sonneville, Antony (FR); Florence L'Alloret, Paris (FR)

(73) Assignee: L'Oreal, Paris (FR)

( * ) Notice: Subject to any disclaimer, the term of this patent is extended or adjusted under 35 U.S.C. 154(b) by 1259 days.

This patent is subject to a terminal disclaimer.

(21) Appl. No.: 10/813,013

(22) Filed: Mar. 31, 2004

(65) Prior Publication Data

US 2005/0002891 A1    Jan. 6, 2005

Related U.S. Application Data

(60) Provisional application No. 60/470,417, filed on May 15, 2003.

(30) Foreign Application Priority Data

Apr. 11, 2003    (FR) .................................. 03 04578

(51) Int. Cl.
*A61Q 1/04*    (2006.01)
*A61Q 1/14*    (2006.01)
*A61Q 5/00*    (2006.01)

(52) U.S. Cl. ........................ 424/401; 424/64; 424/70.11

(58) Field of Classification Search ........................ None
See application file for complete search history.

(56) References Cited

U.S. PATENT DOCUMENTS

| 6,426,062 | B1 | 7/2002 | Chopra et al. |
| 6,645,476 | B1 * | 11/2003 | Morschhauser et al. .... 424/70.1 |
| 6,905,674 | B2 * | 6/2005 | L'Alloret ...................... 424/59 |
| 2004/0141930 | A1 * | 7/2004 | Legrand ...................... 424/62 |

FOREIGN PATENT DOCUMENTS

| EP | 1 069 142 | 1/2001 |
| WO | WO 99/56727 | 11/1999 |
| WO | WO 02/43686 | 6/2002 |

OTHER PUBLICATIONS

U.S. Appl. No. 10/876,570, filed Jun. 28, 2004 L'Alloret.
U.S. Appl. No. 10/813,098, filed Mar. 31, 2004 Aubrun-Sonneville, et al.
U.S. Appl. No. 10/166,128, filed Jun. 11, 2002 L'Alloret, et al.
U.S. Appl. No. 10/270,331, filed Oct. 15, 2002 Lennon, et al.

* cited by examiner

*Primary Examiner*—Jyothsna A Venkat
(74) *Attorney, Agent, or Firm*—Oblon, Spivak, McClelland, Maier & Neustadt, L.L.P.

(57) ABSTRACT

The invention relates to a composition preferably useful for topical application in the form of an oil-in-water emulsion comprising, in a physiologically acceptable medium, an oily phase dispersed in an aqueous phase, containing at least one lipophilic emulsifier and at least one water-soluble or water-dispersible amphiphilic polymer, which may be obtained from 2-acrylamido-2-methylpropanesulphonic acid units and from hydrophobic monomers comprising an oxyalkylene chain.

9 Claims, No Drawings

COMPOSITION CONTAINING AN AMPHIPHILIC POLYMER, USES THEREOF

REFERENCE TO PRIOR APPLICATIONS

This application claims priority to U.S. provisional application 60/470,417 filed May 15, 2003, and to French patent application 0304578 filed Apr. 11, 2003, both incorporated herein by reference.

FIELD OF THE INVENTION

The present invention relates to a composition that preferably is in the form of an oil-in-water emulsion and preferably is suitable for topical application to the skin, lips, etc., comprising an amphiphilic polymer and a lipophilic emulsifier, and to the use of the composition, especially for caring for, removing makeup from and/or cleansing body or facial skin, the hair, the lips and/or the eyes.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous dispersing continuous phase and an oily dispersed discontinuous phase, or of an emulsion of the water-in-oil (W/O) type consisting of an oily dispersing continuous phase and an aqueous dispersed discontinuous phase. O/W emulsions are the ones most sought in the cosmetics field, since they comprise an aqueous phase as external phase, which gives them, when applied to the skin, a fresher, less greasy and lighter feel than W/O emulsions.

Standard O/W emulsions are generally stabilized with amphiphilic molecules of low molar mass (<5000 g/mol), such as emulsifying surfactants of the alkylglycerol or alkylpolyoxyethylene type. However, these surfactants have the drawback of inducing a waxy, heavy feel.

Moreover, it has been envisaged to replace surfactants with amphiphilic polymers, comprising in their chain a hydrophilic portion and a hydrophobic portion consisting of a fatty chain, such as copolymers of a $C_{10}$-$C_{30}$-alkyl acrylate and of acrylic or methacrylic acid, for instance the products sold under the name Pemulen by the company Noveon. However, these polymers thicken the compositions and thus have the drawback of not allowing fluid compositions to be obtained. Moreover, emulsions stabilized with polymers of this type comprise oil drops of relatively large size, which does not allow an acceptable stability to be obtained for low viscosity levels, the instability being reflected especially by rapid creaming, i.e. a rise of oil to the upper part of the emulsion, which is reflected by a phase separation with a white phase at the top of the bottle and an aqueous clear phase at the bottom of the bottle.

In addition, it is known practice from EP-A-1 069 142 to use amphiphilic polymers of α,β-ethylenically unsaturated monomers and of hydrophobic monomers, obtained by free-radical polymerization of a macromonomer containing a hydrophilic block of polyoxyalkylene type and a hydrophobic block containing from 1 to 30 carbon atoms, these polymers possibly being used as thickeners, emulsifiers, dispersants and suspension agents, especially in cosmetics. However, the polymers illustrated in the said document do not produce O/W emulsions with cosmetic properties that are very pleasant for the user while at the same time being very stable and easy to produce.

There is thus still a need to produce O/W emulsions based on amphiphilic polymers, which overcome the difficulties of the prior art, i.e. which are particularly advantageous in terms of cosmetic feel, while at the same time being easy to produce and having good stability.

DETAILED DESCRIPTION OF THE PREFERRED EMBODIMENTS

The inventors have discovered, unexpectedly, that a combination of at least one of a group of particular amphiphilic polymers with at least one of a group of particular lipophilic emulsifiers makes it possible to produce such emulsions. Oil-in-water emulsions that are pleasant to use, which remain stable over time at room temperature or at higher temperatures, may thus be obtained.

Thus, the present invention relates to a composition preferably in a form suitable for topical application, and preferably in the form of an oil-in-water emulsion comprising an oily phase dispersed in an aqueous phase, the composition comprising at least one lipophilic emulsifier and at least one amphiphilic polymer comprising (A) 80 mol % to 99 mol % of 2-acrylamido-2-methylpropanesulphonic acid units of formula (I):

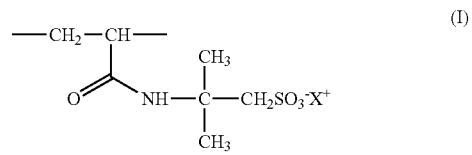

in which $X^+$ is a proton, an alkali metal cation, an alkaline-earth metal cation or an ammonium ion; and (B) 1 mol % to 20 mol % of at least one unit of formula (II) below:

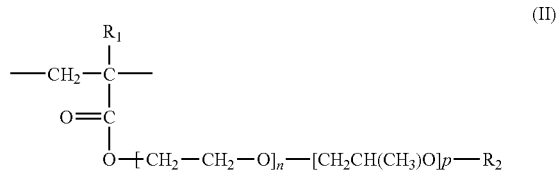

in which n and p, independently of each other, denote an integer ranging from 0 to 30, preferably from 1 to 25 and more preferably from 3 to 20, with the proviso that n+p is less than or equal to 30, preferably less than 25 and better still less than 20; $R_1$ denotes a hydrogen atom or a linear or branched alkyl radical containing from 1 to 6 carbon atoms, and preferably a methyl radical, and $R_2$ denotes a linear or branched alkyl radical containing from 6 to 15 carbon atoms and preferably from 8 to 15 carbon atoms.

The molar proportion of hydrophobic monomer of formula (II) corresponds to the degree of grafting of the polymers.

The term "topical application" means herein an external application to keratin materials, which are especially the skin, the scalp, the eyelashes, the eyebrows, the nails, mucous membranes and the hair.

Since the composition according to the invention is preferably intended for topical application, it preferably contains a physiologically acceptable medium, i.e. a medium that is compatible with the skin, mucous membranes, the hair and the scalp.

The composition of the invention preferably has a uniform texture and is pleasant to apply. In addition, it is advantageously particularly stable on storage. The term "stable" refers to a composition which, after storage for 2 months or more at all temperatures between 4° C. and 50° C., shows neither any macroscopic change in colour, odour or viscosity, nor any variation in pH or change in microscopic appearance.

The composition of the invention has a viscosity that can vary within a wide range depending on the desired final aim. Thus, its viscosity can range, for example, from 0.005 Pa.s to 1 Pa.s at a temperature of 25° C. for a shear rate of 200 $s^{-1}$.

Polymers

The amphiphilic polymer used in the composition of the invention is water-soluble or water-dispersible. The expression "water-soluble or water-dispersible polymer" means a polymer which, when introduced into water at a concentration equal to 1% by weight, gives a macroscopically homogeneous solution whose light transmittance, at a wavelength equal to 500 nm, through a sample 1 cm thick, is at least 10%, which corresponds to an absorbance [abs=−log(transmittance)] of less than 1.5.

The aqueous polymer solutions used according to the invention generally have, at a polymer concentration of 1% by weight, a viscosity of less than 1 Pa.s for a shear rate equal to 1 $s^{-1}$, the viscosity being measured at 25° C. using an RS 150 controlled-stress rheometer (Haake).

The amphiphilic polymers in accordance with the invention generally have a number-average molecular weight ranging from 50,000 to 10,000,000, preferably from 100,000 to 8,000,000 and more preferably from 100,000 to 7,000,000.

The preferred polymers used according to the invention are non-crosslinked polymers that comprise from (A) 80 mol % to 99 mol % and preferably from 85 mol % to 99 mol % of 2-acrylamido-2-methylpropanesulphonic acid units of formula (I) above and from 1 mol % to 20 mol % and preferably from 1 mol % to 15 mol % of units of formula (II) above. In formula (II), the sum of n+p can range from 0 to 30, preferably from 0 to 25 and better still from 0 to 20. The polymers that are particularly preferred are obtained from AMPS units of formula (I) and from units of formula (II) in which p=0; $R_1$ is a methyl radical ($CH_3$); n is an integer ranging from 8 to 25 and $R_2$ is a $C_{12}$-$C_{15}$ alkyl radical.

The polymers for which $X^+$ in formula (I) denotes sodium or ammonium are more particularly preferred.

The amphiphilic polymers used according to the invention can be obtained according to a standard free-radical polymerization processes in the presence of one or more initiators such as, for example, azobisisobutyronitrile (AIBN), azobisdimethyl-valeronitrile, 2,2-azobis[2-amidinopropane]hydrochloride (ABAH), organic peroxides such as dilauryl peroxide, benzoyl peroxide, tert-butyl hydroperoxide, etc., mineral peroxide compounds such as potassium persulphate or ammonium persulphate, or $H_2O_2$ optionally in the presence of reducing agents.

The polymers can be obtained especially by free-radical polymerization in tert-butanol medium in which they precipitate. Using precipitation polymerization in tert-butanol, it is possible to obtain a size distribution of the polymer particles that is particularly favourable for its uses.

The polymerization reaction may be performed at a temperature of between 0 and 150° C., preferably between 10 and 100° C., either at atmospheric pressure or under reduced pressure. It may also be performed under inert atmosphere, and preferably under nitrogen.

According to this process, it is possible to obtain the polymer prepared from 2-acrylamido-2-methylpropanesulphonic acid (AMPS) or a sodium or ammonium salt thereof with an acrylic acid or a methacrylic acid ester and a $C_{11}$ oxo alcohol oxyethylenated with 8 mol of ethylene oxide (Genapol® UD-080 from the company Hoechst/Clariant), a $C_{11}$ oxo alcohol oxyethylenated with 7 mol of ethylene oxide (Genapol® UD-070 from the company Hoechst/Clariant), a $C_{12}$-$C_{14}$ alcohol oxyethylenated with 7 mol of ethylene oxide (Genapol® LA-070 from the company Hoechst/Clariant), a $C_{12}$-$C_{14}$ alcohol oxyethylenated with 9 mol of ethylene oxide (Genapol® LA-090 from the company Hoechst/Clariant), a $C_{12}$-$C_{14}$ alcohol oxyethylenated with 11 mol of ethylene oxide (Genapol® LA-110 from the company Hoechst/Clariant), a $C_{12}$-$C_{15}$ alcohol oxyethylenated with 23 mol of ethylene oxide.

According to one preferred embodiment of the invention, the amphiphilic polymer used is preferably a copolymer of AMPS and of a $C_{12}$-$C_{14}$ or $C_{12}$-$C_{15}$ alkyl methacrylate comprising 7 or 23 oxyethylene groups, obtained from methacrylic acid or a methacrylic acid salt and from Genapol LA-070 or a $C_{12}$-$C_{15}$ alcohol oxyethylenated with 23 mol of ethylene oxide.

Even more preferably, the amphiphilic polymers used are copolymers of AMPS and of an alkyl methacrylate having the following characteristics:

| Name of the pendent chains | $R_3$ | n | Molar proportion of monomer of formula (II) |
|---|---|---|---|
| Genapol LA-070 | Linear $C_{12-14}$ alkyl chain | 7 | 8.5% |
| Genapol LA-070 | Linear $C_{12-14}$ alkyl chain | 7 | 18.8% |
| $C_{12}$-$C_{15}$ alcohol oxyethylenated with 23 mol of ethylene oxide | Branched $C_{12-15}$ alkyl chain | 23 | 10.5% |

The amount (in terms of active material) of amphiphilic polymer(s) in the composition of the invention is not limited and may range, for example, in terms of active material, from 0.01% to 10% by weight, preferably from 0.05% to 10% by weight, better still from 0.05% to 5% by weight and even better still from 0.25% to 3% by weight relative to the total weight of the composition.

Lipophilic Emulsifiers

The composition according to the invention contains one or more lipophilic emulsifiers. These emulsifiers are characterized by an HLB (hydrophilic-lipophilic balance) of less than or equal to 12. They may be chosen, without limitation, from emulsifiers that are soluble or dispersible in fatty substances such as alkanes, esters, ethers, triglycerides and/or silicone oils. They may be chosen especially from polyol esters or ethers; fatty alcohols; esters or ethers comprising a sugar unit; silicone emulsifiers; and mixtures thereof.

Among the polyol esters or ethers that may especially be mentioned are glycerol esters, poly-ethylene glycol esters, sorbitan esters, and mixtures thereof, for example glyceryl monoisostearate, such as the product sold under the name Peceol Isostearique by the company Gattefosse, PEG-8 isostearate, such as the product sold under the name Prisorine 3644 by the company Uniqema, sorbitan isostearate, such as the product sold under the name Arlacel 987 by the company ICI, sorbitan glyceryl isostearate, such as the product sold under the name Arlacel 986 by the company ICI, and mixtures thereof.

Fatty alcohols that may be mentioned include fatty alcohols containing from 8 to 26 carbon atoms, for instance cetyl alcohol, stearyl alcohol and the mixture thereof (cetearyl alcohol), octyldodecanol, 2-butyloctanol, 2-hexyldecanol, 2-undecylpentadecanol and oleyl alcohol, and mixtures thereof.

An example of a sugar ester that may be mentioned is methylglucose isostearate.

Examples of silicone emulsifiers that may be mentioned include dimethicone copolyols, such as the mixture of cyclomethicone and of dimethicone copolyol, sold under the name "DC 5225 C" by the company Dow Corning, and alkyldimethicone copolyols, such as laurylmethicone copolyol sold under the name "Dow Corning 5200 Formulation Aid" by the company Dow Corning and cetyldimethicone copolyol sold under the name ABIL EM 90 by the company Goldschmidt, or the polyglyceryl-4 isostearate/cetyl dimethicone copolyol/hexyl laurate mixture sold under the name ABIL WE 09 by the company Goldschmidt.

According to one preferred embodiment of the invention, the lipophilic emulsifier is chosen from glyceryl esters, polyethylene glycol esters and fatty alcohols, and mixtures thereof.

The amount (in terms of active material) of lipophilic emulsifier(s) is not particularly limited and can generally range, for example, from 0.01% to 10% by weight, preferably from 0.05% to 5% by weight and better still from 0.1% to 2.5% by weight relative to the total weight of the composition.

The lipophilic emulsifier is generally introduced into the oily phase of the emulsion.

Aqueous Phase

Advantageously, the amphiphilic polymer is introduced into the aqueous phase of the emulsion. In addition, the aqueous phase contains water and optionally one or more water-miscible or at least partially water-miscible compounds, for instance polyols; $C_2$ to $C_8$ lower monoalcohols, such as ethanol and isopropanol; and $C_3$ to $C_4$ ketones that are liquid at room temperature. The term "room temperature" should be understood as meaning a temperature of about 25° C., at normal atmospheric pressure (760 mmHg).

The term "polyol" should be understood as meaning any organic molecule comprising at least two free hydroxyl groups. Examples of polyols that may be mentioned include glycols, for instance butylene glycol, propylene glycol, and isoprene glycol, glycerol and polyethylene glycols, for instance PEG-8, sorbitol and sugars, for instance glucose.

The aqueous phase may also comprise any common water-soluble or water-dispersible additive, including those as mentioned below.

The aqueous phase is not particularly limited and may represent from 10% to 99% by weight, preferably from 20% to 95% by weight, better still from 30% to 90% by weight and even better still from 40% to 85% by weight relative to the total weight of the composition.

The water-miscible compound(s), such as lower polyols and alcohols, are not generally limited and may be present in an amount ranging from, e.g., 0 to 30%, especially from 0.1% to 30% and better still in an amount ranging from 1% to 20%, relative to the total weight of the composition.

Oily Phase

The nature of the oily phase of the emulsion according to the invention is not critical. The oily phase is a fatty phase containing at least one fatty substance chosen from volatile or non-volatile oils that are liquid at room temperature (20-25° C.), gums and pasty fatty substances of animal, plant, mineral or synthetic origin, and mixtures thereof. These fatty substances are physiologically acceptable.

The oily phase generally comprises the lipophilic emulsifier and it may also comprise any common liposoluble or lipodispersible additive as mentioned below.

The oily phase contains at least one oil, more particularly at least one cosmetic oil. The term "oil" means a fatty substance that is liquid at room temperature (25° C.).

As oils that may be used in the composition of the invention, examples that may be mentioned include:

hydrocarbon-based oils of animal origin, such as perhydrosqualene;

hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil and shea butter oil;

synthetic esters and ethers, especially of fatty acids, for instance the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, for instance purcellin oil, isononyl isononanoate, isopropyl myristate, 2-ethylhexyl palmitate, 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

linear or branched hydrocarbons of mineral or synthetic origin, such as volatile or non-volatile liquid paraffins, and derivatives thereof, petroleum jelly, polydecenes, isohexadecane, isododecane, and hydrogenated polyisobutene such as Parleam® oil;

partially hydrocarbon-based and/or silicone-based fluoro oils, for instance those described in document silicone oils, for instance volatile or non-volatile polymethylsiloxanes (PDMSs) containing a linear or cyclic silicone chain, which are liquid or pasty at room temperature, especially volatile silicone oils, in particular cyclopolydimethylsiloxanes (cyclomethicones) such as cyclohexadimethylsiloxane and cyclo-pentadimethylsiloxane; polydimethylsiloxanes comprising alkyl, alkoxy or phenyl groups, which are pendent or at the end of a silicone chain, these groups containing from 2 to 24 carbon atoms; phenylsilicones, for instance phenyltrimethicones, phenyldimethicones, phenyltrimethylsiloxydiphenylsiloxanes, diphenyl-dimethicones, diphenylmethyldiphenyltrisiloxanes, 2-phenylethyltrimethylsiloxysilicates and polymethylphenylsiloxanes;

mixtures thereof.

According to one preferred embodiment, the composition of the invention comprises at least one oil chosen from silicone oils, linear or branched hydrocarbons, synthetic ethers and esters, and mixtures thereof and is especially chosen from volatile silicone oils and branched hydrocarbons, for instance Parleam® oil, and mixtures thereof.

The other fatty substances that may be present in the oily phase are, for example, fatty acids containing from 8 to 30 carbon atoms, for instance stearic acid, lauric acid or palmitic acid; waxes; gums such as silicone gums (dimethiconol); silicone resins such as trifluoromethyl-$C_{1-4}$-alkyldimethicone and trifluoropropyldimethicone, and silicone elastomers, for instance the products sold under the names "KSG" by the company Shin-Etsu, under the name "Trefil" by the company Dow Corning or under the name "Gransil" by the company Grant Industries, and mixtures thereof.

These fatty substances may be chosen in a varied manner by a person skilled in the art in order to prepare a composition having the desired properties, for example in terms of consistency or texture.

The amount of oily phase in the composition of the invention is not particularly limited and may range for example from 1% to 90% by weight, preferably from 5% to 80% by weight, better still from 10% to 70% by weight and even better still from 15% to 60% by weight relative to the total weight of the composition.

Additives

The composition of the invention may also contain one or more adjuvants, including for example those that are common in cosmetics or dermatology. Adjuvants that may be mentioned in particular include gelling agents, active agents, preserving agents, antioxidants, fragrances, solvents, salts, fillers, sunscreens (=UV-screening agents), dyestuffs, basic agents (triethanolamine, diethanolamine or sodium hydroxide) or acidic agents (citric acid), and also lipid vesicles or any other type of vector (nanocapsules, microcapsules, etc.), hydrophilic surfactants, and mixtures thereof. These adjuvants are used in the usual proportions in the cosmetics field, for example from 0.01% to 30% of the total weight of the composition, and, depending on their nature, they are introduced into the aqueous phase of the composition or into the oily phase, or alternatively into vesicles or any other type of vector. These adjuvants and the concentrations thereof must be such that they do not modify the desired property for the emulsion of the invention.

Depending on the desired viscosity of the composition according to the invention, it is possible to incorporate therein one or more hydrophilic or lipophilic gelling agents. Examples of hydrophilic gelling agents that may be mentioned include modified or unmodified carboxyvinyl polymers, such as the products sold under the names Carbopol (INCI name: carbomer) and Pemulen (INCI name: Acrylates/C10-30 alkyl acrylate crosspolymer) by the company Noveon; polyacrylamides; optionally crosslinked and/or neutralized 2-acrylamido-2-methylpropane sulphonic acid polymers and copolymers, for instance the poly(2-acrylamido-2-methylpropanesulphonic acid) sold by the company Hoechst under the name "Hostacerin AMPS" (INCI name: ammonium polyacryldimethyltauramide); crosslinked anionic copolymers of acrylamide and of AMPS, which are in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by the company SEPPIC; polysaccharide biopolymers, for instance guar gum, alginates and modified or unmodified celluloses; and mixtures thereof. When they are present, these gelling agents must be introduced in an amount such that they do not modify the properties of the composition according to the invention. Lipophilic gelling agents that may especially be mentioned include modified clays such as modified magnesium silicate (Bentone Gel VS38 from Rheox), or hectorite modified with distearyldimethylammonium chloride (CTFA name: Disteardimonium hectorite) sold under the name Bentone 38 CE by the company Rheox.

As fillers that may be used in the composition of the invention, examples that may be mentioned include the pigments such as titanium oxide, zinc oxide or iron oxide and organic pigments; kaolin; silica; talc; boron nitride; organic spherical powders, fibres; and mixtures thereof. Examples of organic spherical powders that may be mentioned include polyamide powders and especially Nylon® powders such as Nylon-1 or Polyamide 12, sold under the name Orgasol by the company Atochem; polyethylene powders; Teflon®; microspheres based on acrylic copolymers, such as those made of ethylene glycol dimethacrylate/lauryl methacrylate copolymer, sold by the company Dow Corning under the name Polytrap; expanded powders such as hollow microspheres and especially the microspheres sold under the name Expancel by the company Kemanord Plast or under the name Micropearl F 80 ED by the company Matsumoto; silicone resin microbeads such as those sold under the name Tospearl by the company Toshiba Silicone; polymethyl methacrylate microspheres, sold under the name Microsphere M-100 by the company Matsumoto or under the name Covabead LH85 by the company Wackherr; ethylene acrylate copolymer powders, such as those sold under the name Flobeads by the company Sumitomo Seika Chemicals; powders of natural organic materials such as starch powders, especially of maize starch, wheat starch or rice starch, which may or may not be crosslinked, such as the starch powders crosslinked with octenyl succinate anhydride, sold under the name Dry-Flo by the company National Starch. Examples of fibres that may be mentioned include polyamide fibres, especially such as Nylon 6 (or Polyamide 6) (INCI name: Nylon 6) fibres, Nylon 6,6 (or Polyamide 66) (INCI name: Nylon 66) fibres, or such as poly-p-phenyleneterephthamide fibres; and mixtures thereof. These fillers may be present in amounts ranging from 0 to 20% by weight and preferably from 0.5% to 10% by weight relative to the total weight of the composition.

As active agents that may be used in the composition of the invention, examples that may be mentioned include enzymes (for example lactoperoxidase, lipase, protease, phospholipase and cellulases); flavonoids; moisturizers such as protein hydrolysates; sodium hyaluronate; polyols, for instance glycerol, glycols, for instance polyethylene glycols, and sugar derivatives; anti-inflammatory agents; procyannidol oligomers; vitamins, for instance vitamin A (retinol), vitamin E (tocopherol), vitamin K, vitamin C (ascorbic acid), vitamin B5 (panthenol), vitamin B3 or PP (niacinamide), derivatives of these vitamins (especially esters) and mixtures thereof; keratolytic agents and/or desquamating agents, such as salicylic acid and its derivatives, α-hydroxy acids, for instance lactic acid and glycolic acid and derivatives thereof, and ascorbic acid and its derivatives; urea; caffeine; depigmenting agents such as kojic acid, hydroquinone and caffeic acid; salicylic acid and its derivatives; retinoids such as carotenoids and vitamin A derivatives; hydrocortisone; melatonin; algal extracts, fungal extracts, plant extracts, yeast extracts or bacterial extracts; steroids; antibacterial active agents, for instance 2,4,4'-trichloro-2'-hydroxy-diphenyl ether (or triclosan), 3,4,4'-trichloro-carbanilide (or triclocarban) and the acids indicated above, and especially salicylic acid and its derivatives; tensioning agents such as synthetic polymers, plant proteins, polysaccharides of plant origin optionally in the form of microgels, starches, wax dispersions, mixed silicates and colloidal particles of mineral fillers; ceramides; anti-inflammatory agents; calmatives; mattifying agents; agents for preventing hair loss and/or for promoting regrowth of the hair; anti-wrinkle agents; essential oils; and mixtures thereof; and any active agent that is suitable for the final aim of the composition.

Examples of steroids that may be mentioned include dehydroepiandrosterone (or DHEA), and also (1) its precursors and biological derivatives, in particular the salts and esters of DHEA, such as DHEA sulphate and salicylate, 7-hydroxy DHEA, 7-keto DHEA, 7-hydroxy and 7-keto DHEA esters, especially 3-β-acetoxy-7-oxo DHEA, and (2) its precursors and chemical derivatives, in particular sapogenins such as diosgenin or hecogenin, and/or derivatives thereof such as hecogenin acetate, and/or natural extracts containing them and especially extracts of Dioscorea plants, such as wild yam.

The UV-screening agents may be organic or mineral (or physical UV sunblocks). They may be present in an active-material amount ranging from 0.01% to 20% by weight of active material, preferably from 0.1% to 15% by weight and better still 0.2% to 10% by weight relative to the total weight of the composition.

As examples of UV-A-active and/or UV-B-active organic screening agents that may be added to the composition of the invention, examples that may be mentioned include derivatives containing a sulphonic function, such as sulphone-containing or sulphonate-containing derivatives of benzylidenecamphor, of benzophenone or of phenylbenzimidazole, more particularly benzylidenecamphor derivatives, for instance benzene-1,4-bis(3-methylidenecamphor-10-sulphonic acid) (INCI name: Terephthalylidenedicamphor-sulphonic acid) manufactured under the name "Mexoryl SX" by the company Chimex, 3-benzylidenecamphor-4'-sulphonic acid (INCI name: Benzylidenecamphorsulphonic acid), manufactured under the name "Mexoryl SL" by the company Chimex, 2-[4-(camphormethylidene)phenyl]benz-imidazole-5-sulphonic acid and phenylbenzimidazole-sulphonic acid (INCI name: Phenylbenzimidazolesulphonic acid), sold under the name Eusolex 232 by the company Merck; para-aminobenzoic acid derivatives; salicylic derivatives such as ethylhexyl salicylate sold under the trade name Neo Heliopan OS by Haarmann & Reimer; dibenzoylmethane derivatives such as butylmethoxydibenzoylmethane sold especially under the trade name Parsol 1789 by Hoffmann La Roche; cinnamic derivatives such as ethylhexyl methoxycinnamate sold especially under the trade name Parsol MCX by Hoffmann La Roche; β,β'-diphenylacrylate derivatives such as octocrylene (2-ethylhexyl α-cyano-β,β-diphenylacrylate) sold under the trade name Uvinul N539 by the company BASF; benzophenone derivatives such as Benzophenone-1 sold under the trade name Uvinul 400 by BASF, Benzophenone-2 sold under the trade name Uvinul D50 by BASF, Benzophenone-3 or Oxybenzone, sold under the trade name Uvinul M40 by BASF, Benzophenone-4 sold under the trade name Uvinul MS40 by BASF; benzylidene-camphor derivatives such as 4-methylbenzylidenecamphor sold under the trade name Eusolex 6300 by Merck; phenylbenzimidazole derivatives such as Benzimidazilate sold under the trade name Neo Heliopan AP by Haarmann & Reimer; triazine derivatives such as Anisotriazine sold under the trade name Tinosorb S by Ciba Geigy and ethylhexyltriazone sold especially under the trade name Uvinul T150 by BASF; phenylbenzotriazole derivatives such as Drometrizole Trisiloxane sold under the trade name Silatrizole by Rhodia Chimie and methylenebis-benzotriazolyl-tetramethylbutylphenol, sold in solid form under the trade name Mixxim BB/100 by Fairmount Chemical, or in micronized form as an aqueous dispersion under the trade name Tinosorb M by Ciba Specialty Chemicals; anthranilic derivatives such as menthyl anthranilate sold under the trade name Neo Heliopan MA by Haarmann & Reimer; imidazoline derivatives; benzalmalonate derivatives; and mixtures thereof.

As physical sunblocks that may be added to the composition of the invention, examples that may be mentioned include pigments and nanopigments of coated or uncoated metal oxides, especially titanium oxide, iron oxide, zirconium oxide, zinc oxide or cerium oxide, and mixtures thereof, these oxides possibly being in the form of optionally coated microparticles or nanoparticles (nanopigments).

The compositions of the invention can be prepared according to usual processes for the preparation of, e.g., O/W emulsions. The amphiphilic AMPS copolymer is dissolved with stirring in the aqueous phase, preferably at room temperature (25° C.), and the emulsion is prepared by introducing the oily phase into the aqueous phase with stirring.

The compositions according to the invention may be, for example, in any of the galenical forms of O/W emulsions, for example in the form of a serum, a milk or a cream, and they are prepared according to the usual methods. The compositions that are the subject of the invention are intended for topical application and can especially constitute a dermatological or cosmetic composition intended, for example, for caring for, treating, cleansing and making up keratin materials, and especially human skin, lips, hair, eyelashes and nails.

According to one preferred embodiment of the invention, the composition constitutes a cosmetic composition and is intended for topical application to the skin.

Thus, a subject of the invention is also the cosmetic use of a cosmetic composition as defined above, for caring for, removing makeup from and/or cleansing the skin, the lips and/or the hair.

Finally, a subject of the invention is a cosmetic process for treating the skin, including the scalp, the hair and/or the lips, characterized in that a cosmetic composition as defined above is applied to the skin, the hair and/or the lips.

The examples that follow will allow the invention to be understood more clearly, without, however, being limiting in nature. Unless otherwise mentioned, the amounts indicated are percentages by weight.

I. EXAMPLES ACCORDING TO THE INVENTION

Example 1 According to the Invention

Milk

| Oily phase: | |
|---|---|
| Cyclohexadimethylsiloxane | 6% |
| Parleam ® oil | 9% |
| Glyceryl isostearate (Peceol Isostearique from Gattefosse) | 0.5% |
| Aqueous phase: | |
| Copolymer of AMPS and of Genapol LA-070 methacrylate (with 8.5 mol % of monomer of formula II) | 1% |
| Triethanolamine as an aqueous 10% solution | 0.06% |
| Preserving agents | 1% |
| Water | 82.44% |

Procedure: The AMPS-based polymer is dissolved in the aqueous phase for 2 hours at room temperature with mechanical stirring. The oily phase is then introduced into the aqueous phase with stirring using a Moritz homogenizer at a speed of 4000 rpm for 20 minutes at 25° C.

The composition obtained is in the form of a stable fluid milk of pH 6.6, with a viscosity of 1.7 poises (170 mPa·s), the viscosity of the milk being measured using a Rheomat 180 machine at 25° C. at a shear rate of 200 $s^{-1}$ using a No. 2 spindle.

Example 2 According to the Invention

Milk

| Oily phase: | |
|---|---|
| Cyclohexadimethylsiloxane | 6% |
| Parleam ® oil | 9% |
| PEG-8 isostearate (Prisorine 3644 from the company Uniqema) | 0.5% |
| Aqueous phase: | |
| Copolymer of AMPS and of Genapol LA-070 methacrylate (with 8.5 mol % of monomer of formula II) | 1% |
| Triethanolamine as an aqueous 10% solution | 0.06% |
| Preserving agents | 1% |
| Water | 82.44% |

The procedure is identical to that of Example 1.

The composition obtained is in the form of a stable fluid milk of pH 6.6, with a viscosity of 3.3 poises (330 mPa·s), the viscosity of the milk being measured using a Rheomat 180 machine at 25° C. at a shear rate of 200 $s^{-1}$ using a No. 2 spindle.

Example 3 According to the Invention

Milk

| Oily phase: | |
|---|---|
| Cyclohexadimethylsiloxane | 6% |
| Parleam ® oil | 9% |
| Glyceryl isostearate (Peceol Isostearique from Gattefosse) | 0.5% |
| Aqueous phase: | |
| Copolymer of AMPS and of Genapol LA-070 methacrylate (with 18.8 mol % of monomer of formula II) | 1% |
| Triethanolamine as an aqueous 10% solution | 0.06% |
| Preserving agents | 1% |
| Water | 82.44% |

The procedure is identical to that of Example 1.

The composition obtained is in the form of a stable fluid milk.

Example 4 According to the Invention

Cream

| Oily phase: | |
|---|---|
| Cyclopentadimethylsiloxane | 16% |
| Parleam ® oil | 12.8% |
| Liquid fraction of shea butter | 2% |
| Tocopheryl acetate | 0.2% |
| Octyl palmitate | 3% |
| Cetyl alcohol | 3% |
| Stearyl alcohol | 3% |
| Propyl paraben | 0.1% |
| Aqueous phase: | |
| Copolymer of AMPS and of Genapol LA-070 methacrylate (8.5 mol % of monomer of formula II) | 0.8% |
| Triethanolamine | 0.011% |
| Glycerol | 5% |
| Preserving agents | 0.5% |
| Water | qs 100% |

Procedure: The AMPS-based polymer is dissolved in the aqueous phase for 2 hours at room temperature with mechanical stirring. The oily phase, preheated to 70° C., is then introduced into the aqueous phase, which is also heated to 70° C., with stirring using a Moritz homogenizer at a speed of 4000 rpm for 20 minutes. Stirring is continued until the emulsion is cooled to 25° C.

The formula is in the form of a cream (pH~6.9). Its viscosity, measured using a Rheomat 180 machine at 25° C. at a shear rate of 200 $s^{-1}$ with a No. 3 spindle, is 1.31 Pa.s. The emulsion was subjected to an accelerated-ageing test by centrifugation (Optima TLX Ultracentrifuge) at a speed of 25,000 rpm for 5 minutes. After this test, the emulsion remained stable.

II. COMPARATIVE EXAMPLES

Comparative Example 1

Milk

| Oily phase: | |
|---|---|
| Cyclohexadimethylsiloxane | 6% |
| Parleam ® oil | 9% |
| Aqueous phase: | |
| Copolymer of AMPS and of Genapol LA-070 methacrylate (with 8.5 mol % of monomer of formula II) | 1% |
| Triethanolamine as an aqueous 10% solution | 0.06% |
| Preserving agents | 1% |
| Water | 82.94% |

The procedure is identical to that of Example 1.

The composition obtained is an unstable fluid milk, since it undergoes creaming, i.e. a rise of oil to the upper part of the emulsion, which is reflected by a phase separation with a white phase at the top of the bottle and an aqueous clear phase at the bottom of the bottle.

This comparative example shows that the presence of lipophilic surfactant is essential for obtaining a stable fluid composition.

Comparative Example 2

Milk

| Oily phase: | |
|---|---|
| Cyclohexadimethylsiloxane | 6% |
| Parleam ® oil | 9% |
| Disodium salt of N-stearoylglutamic acid (acylglutamate HS21 from the company Ajinomoto) | 0.5% |
| Aqueous phase: | |
| Copolymer of AMPS and of Genapol LA-070 methacrylate (with 8.5 mol % of monomer of formula II) | 1% |
| Triethanolamine as an aqueous 10% solution | 0.06% |
| Preserving agents | 1% |
| Water | 82.44% |

The procedure is identical to that of Example 1.

The composition obtained is an unstable fluid milk: creaming takes place.

Comparative Example 1 shows that it is essential to have a lipophilic emulsifier, and Comparative Example 2 shows that a hydrophilic emulsifier (HLB>12) such as acylglutamate HS21 does not make it possible to stabilize an O/W emulsion containing the modified AMPS polymer corresponding to the claimed formula.

Comparative Example 3

Cream

| Oily phase: | |
|---|---|
| Cyclopentadimethylsiloxane | 16% |
| Parleam ® oil | 18.8% |
| Liquid fraction of shea butter | 2% |
| Tocopheryl acetate | 0.2% |
| Octyl palmitate | 3% |
| Propyl paraben | 0.1% |
| Aqueous phase: | |
| Copolymer of AMPS and of Genapol LA-070 methacrylate (8.5 mol % of monomer of formula II) | 0.8% |
| Triethanolamine | 0.011% |
| Glycerine | 5% |
| Preserving agents | 0.5% |
| Water | qs 100% |

The procedure is identical to that of Example 1.

The formula is in the form of a cream (pH~6.8). Its viscosity, measured using a Rheomat 180 machine at 25° C. at a shear rate of 200 s$^{-1}$ with a No. 3 spindle, is 0.65 Pa.s. The emulsion was subjected to an accelerated-ageing test by centrifugation (Optima TLX Ultracentrifuge) at a speed of 25,000 rpm for 5 minutes. After this test, the emulsion was found to be unstable (observation of macroscopic phase separation: creaming). This example thus shows the importance of the presence of the lipophilic emulsifier.

The above written description of the invention provides a manner and process of making and using it such that any person skilled in this art is enabled to make and use the same, this enablement being provided in particular for the subject matter of the appended claims, which make up a part of the original description.

As used above, the phrases "selected from the group consisting of," "chosen from," and the like include mixtures of the specified materials.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition in the form of an oil-in-water emulsion comprising an oily phase dispersed in an aqueous phase, at least one lipophilic emulsifier in an amount of 0.01 to 10% by weight relative to the total weight of the composition, wherein the at least one lipophilic emulsifier is selected from the group consisting of glyceryl stearate, PEG-8 isostearate, and sorbitan isostearate, and at least one amphiphilic polymer in an amount of 0.01 to 10% by weight relative to the total weight of the composition, wherein said amphiphilic polymer comprises:

(A) 85 mol % to 99 mol % of 2-acrylamido-2-methylpropanesulphonic acid units of formula (I):

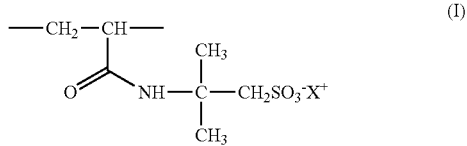

(I)

in which $X^+$ is a proton, an alkali metal cation, an alkaline-earth metal cation or an ammonium ion; and (B) 1 mol % to 15 mol % of units of formula (II):

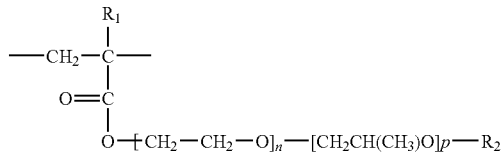

(II)

wherein in formula (II) p=0; $R_1$ is a methyl radical; n is 7 and $R_2$ is a $C_{12}$-$C_{15}$ alkyl radical.

2. The composition according to claim 1, wherein said composition is a cosmetic or dermatological composition.

3. A method for caring for, removing makeup from and/or cleansing the skin, the lips and/or the hair, comprising applying the composition of claim 1 to the skin, the lips and/or the hair.

4. A method for treating the skin, the hair and/or the lips, comprising applying to the skin, the hair and/or the lips the composition of claim 1.

5. The composition according to claim 1, wherein said composition has a viscosity of 0.005 Pa.s to 1 Pa.s at a temperature of 25° C. for a shear rate of 200 $s^{-1}$.

6. The composition according to claim 1, wherein said amphiphilic polymer has a number-average molecular weight of 50,000 to 10,000,000.

7. The composition according to claim 1, wherein said composition is suitable for topical application to the skin, the lips and/or the hair.

8. The composition according to claim 1, wherein said composition is storage stable.

9. The composition according to claim 1, wherein $X^+$ in formula (I) denotes sodium or ammonium.

* * * * *